United States Patent [19]

Okushima et al.

[11] Patent Number: 4,822,797
[45] Date of Patent: Apr. 18, 1989

[54] PIPERAZINYL CARBONYL PHENYL PYRIDAZINONE DERIVATIVES USEFUL AS CARDIOTONICS

[75] Inventors: Hiromi Okushima, Kawasaki; Akihiro Narimatsu, Yokohama; Makio Kobayashi; Rikizo Furuya, both of Tokyo; Yoshimi Kitada, Yokohama, all of Japan

[73] Assignee: Mitsubishi Chemical Industries Limited, Tokyo, Japan

[21] Appl. No.: 26,758

[22] PCT Filed: Feb. 21, 1986

[86] PCT No.: PCT/JP86/00083
§ 371 Date: Mar. 31, 1987
§ 102(e) Date: Mar. 31, 1987

[87] PCT Pub. No.: WO87/05016
PCT Pub. Date: Aug. 27, 1987

[51] Int. Cl.$^4$ .............. C07D 403/10; C07D 405/14; A61K 31/50
[52] U.S. Cl. ..................................... 514/252; 544/238
[58] Field of Search ................. 544/238; 514/252

[56] References Cited

U.S. PATENT DOCUMENTS 4,631,279 12/1986 Robertson .............. 514/247
4,636,504 1/1987 Rossy et al. .............. 514/252
4,639,451 1/1987 Katakami et al. .............. 514/247

FOREIGN PATENT DOCUMENTS 60-197660 10/1985 Japan .

OTHER PUBLICATIONS

Medicinal Chemistry, Alfred Burger, Interscience Publishers Inc., p. 42.

Primary Examiner—Mark L. Berch
Attorney, Agent, or Firm—Oblon, Fisher, Spivak, McCelland & Maier

[57] ABSTRACT

Pyridazinone derivatives represented by the following general formula (I):

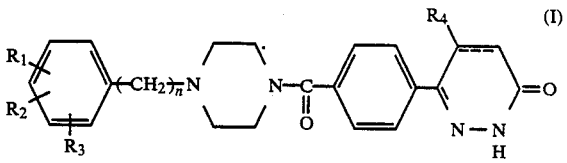

wherein $R_1$, $R_2$ and $R_3$ represent a hydrogen atom, hydroxy group or alkoxy group of not more than 5 carbon atoms, or two of $R_1$, $R_2$ and $R_3$ may be combined together to form a group of —O—CH$_2$—O— or —O—CH$_2$—CH$_2$—O—, $R_4$ represents an alkyl group, n represents an integer of 0 to 4 and the dotted line represents a single or double bond, or salts thereof.

4 Claims, No Drawings

PIPERAZINYL CARBONYL PHENYL PYRIDAZINONE DERIVATIVES USEFUL AS CARDIOTONICS

TECHNICAL FIELD OF THE INVENTION

This invention relates to novel pyridazinone derivatives or salts thereof which are useful as cardiotonic and also have vasodilative activity and blood pressure depressing activity.

BACKGROUND OF THE INVENTION

A cardiotonic directly acts on a heart to enhance the contraction thereof and various pharmaceutical drugs have been used in the treatment of cardiac insufficiency.

However, many of these cardiotonics have defects in that their safety margin is extremely narrow, they may cause arrhythmia, their cardiac stimulating activity is transient and they are not suitable for oral administration.

The present inventors have sought for compounds which are of high activity and capable of showing the sufficiently sustained activity as the cardiotonic and have discovered the present invention.

DISCLOSURES OF THE INVENTION

The gist of the present invention resides in pyridazinone derivatives represented by the following general formula (I):

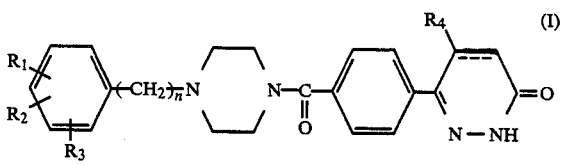

wherein $R_1$, $R_2$ and $R_3$ represent a hydrogen atom, hydroxy group or alkoxy group of not more than 5 carbon atoms, for example, methoxy, ethoxy, propoxy, butoxy, pentyloxy, etc., or two of $R_1$, $R_2$ and $R_3$ may be combined together to form a group of —O—$CH_2$—O— or —O—$CH_2$—$CH_2$—O—, $R_4$ represents an alkyl group, preferably, an alkyl group of not more than 5 carbon atoms, n represents an integer of 0 to 4 and the dotted line represents a single or double bond, or salts thereof.

BEST EMBODIMENTS OF THE INVENTION

The present invention will be explained more in detail hereinafter.

A pyridazinone derivative according to the present invention may be prepared, for example, by the following reaction route:

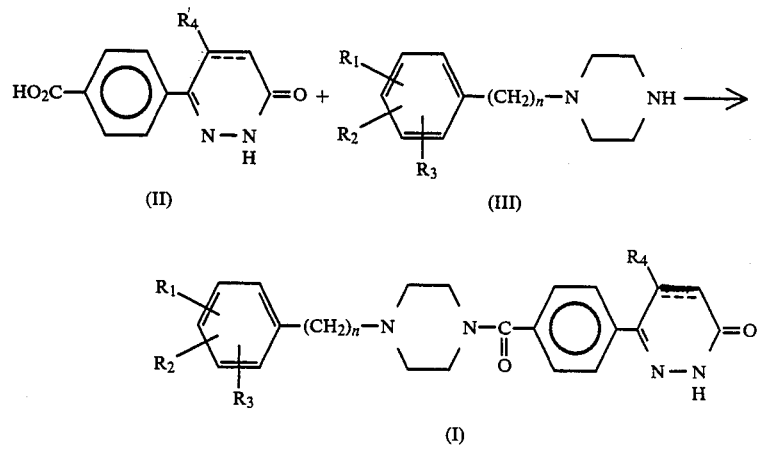

wherein $R_1$, $R_2$, $R_3$ and $R_4$ as well as the dotted line are as defined hereinabove.

That is, the compound of the general formula (I) may be produced by an usual amide coupling between the carboxylic acid (II) or derivative thereof and the amine (III).

For instance, there can be mentioned (A) a mixed acid anhydride method, that is, a method of reacting an alkyl halocarboxylic acid with the carboxylic acid (II) to obtain a mixed acid anhydride and then reacting with the amine (III), (B) a carbodiimide method, that is, a method of condensing the carboxylic acid (II) with the amine (III) under the presence of a dehydrating agent such as dicyclohexyl carbodiimide and, in addition, (C) a caboxylic acid halide method, active ester method and the like, the mixed acid anhydride method above being preferred among them.

The mixed acid anhydride may be prepared by reacting the carboxylic acid (II) with the alkyl halocarboxylic acid under the presence of a basic compound (organic base such as triethylamine, pyridine and diazabicycloundecene (DBU); or inorganic salt such as potassium carbonate and sodium carbonate) in a solvent conventionally used for the mixed acid anhydride mehod, for example, tetrahydrofuran, dioxane, toluene, chloroform, ethyl acetate, dimethy formamide and dimethyl acetoamide or a mixed solvent thereof.

The reaction temperature is of about −20° C. to 100° C. and the reaction time is of about 5 minutes to 10 hours. The resultant mixed acid anhydride may directly be reacted with the amine (III) without further isolation. The reaction with the amine is taken place at −20° C. to 100 ° C. for about 5 minutes to 10 hours.

The carboxylic acid (II) is a known compound as disclosed in Journal of Medicinal Chemistry, Vol 17, p. 281 -286 (1974). The amine (III) is a well known piperazine derivative.

As the pyridazinone derivative according to the present invention obtained by the reaction as described above, there can be mentioned, for example, the following compound:

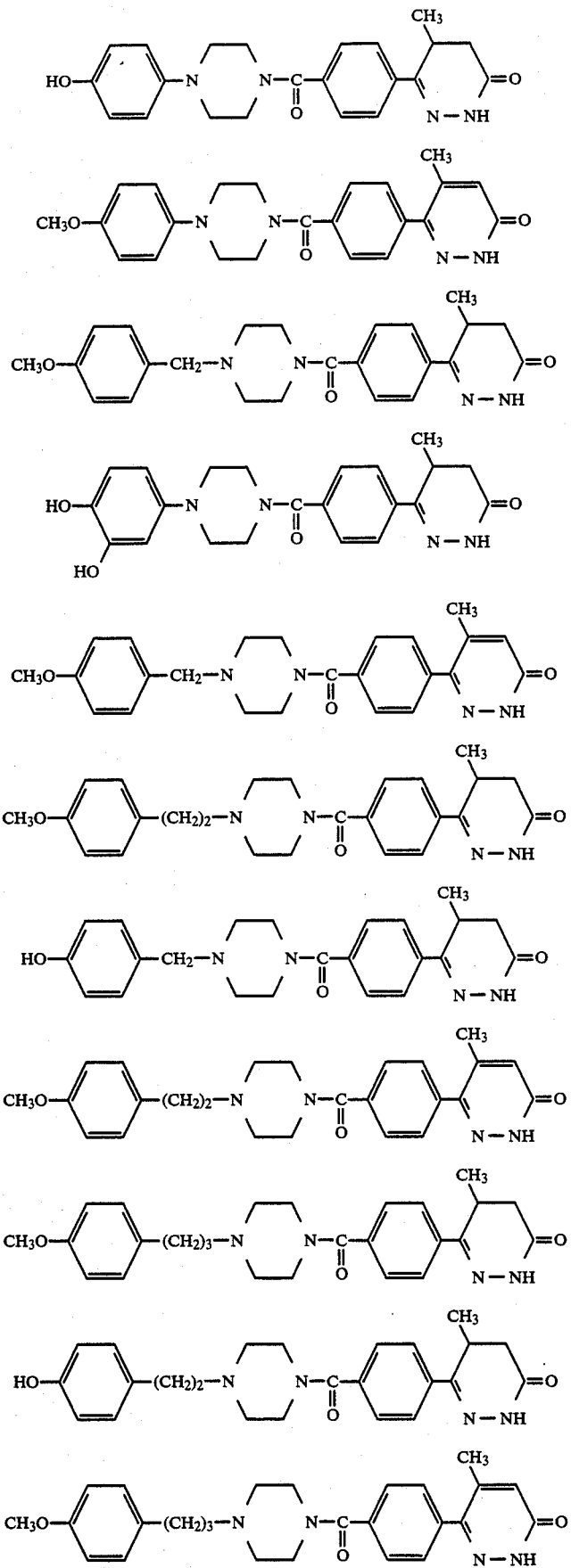

-continued
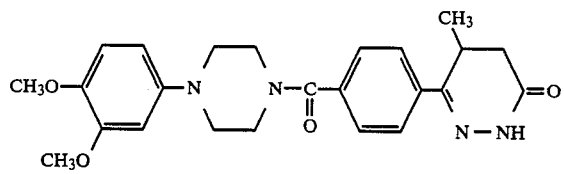
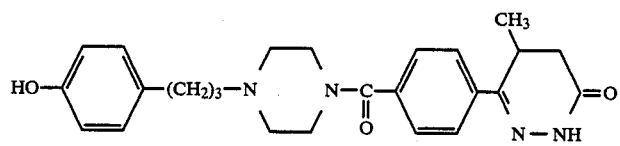
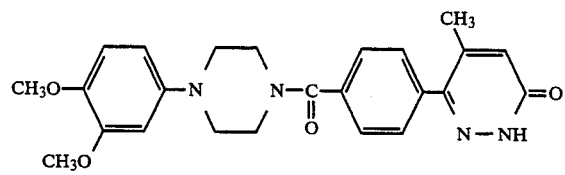
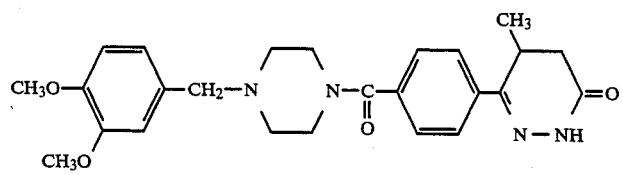
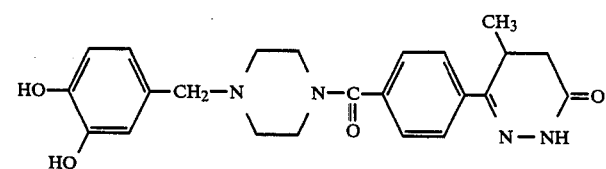
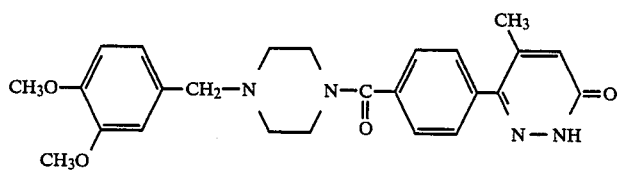
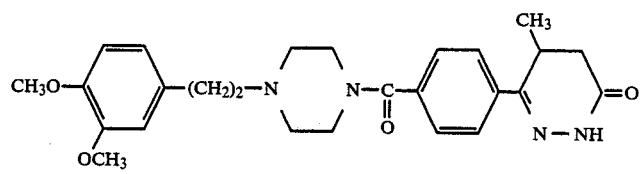
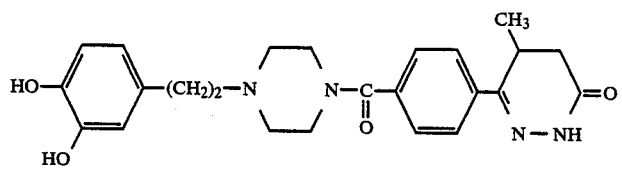
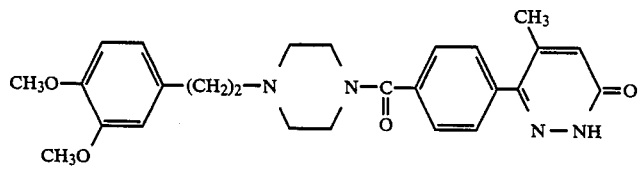

-continued
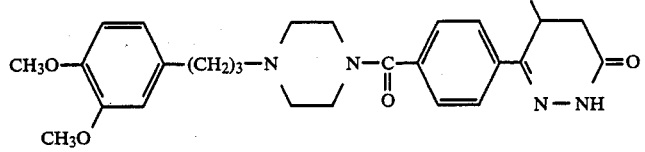
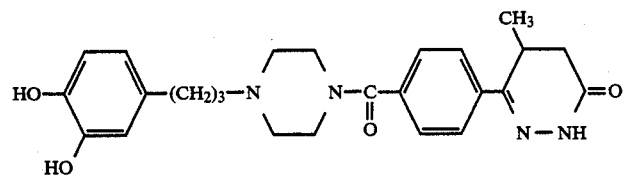
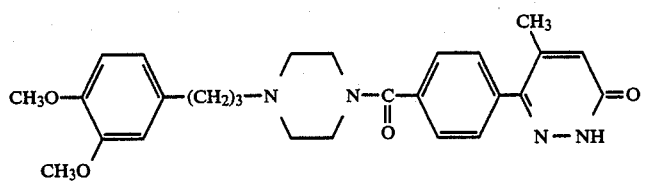
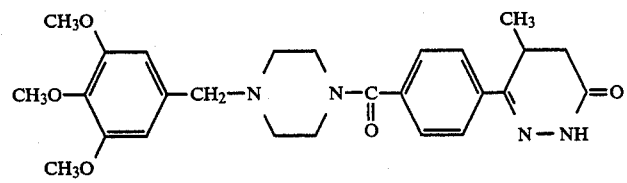
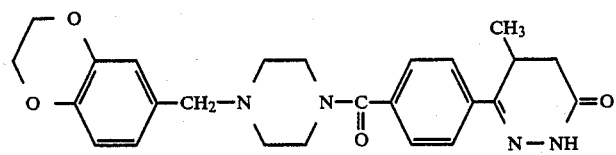
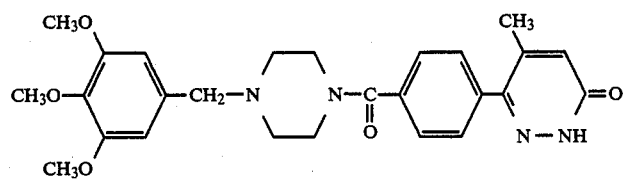
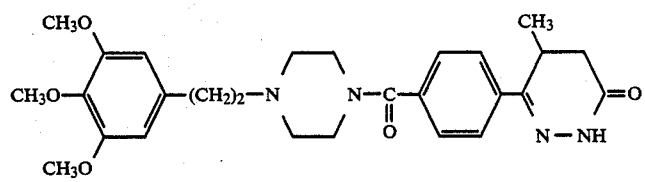
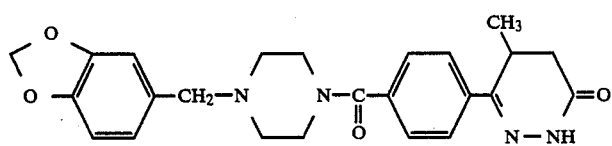
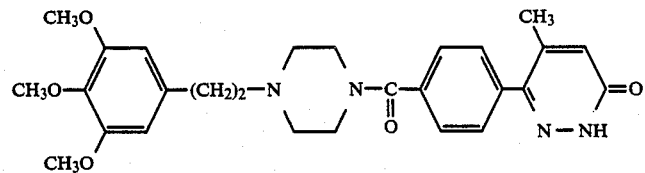

-continued

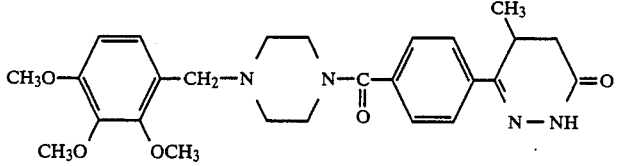

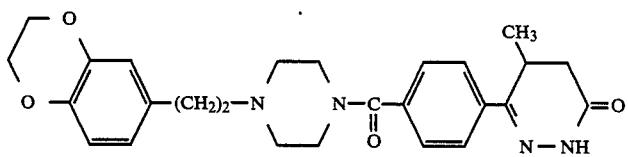

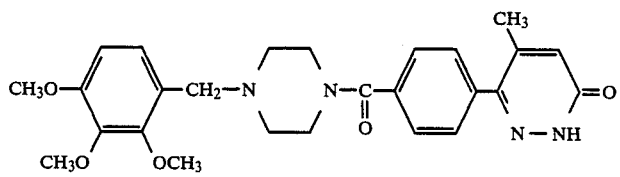

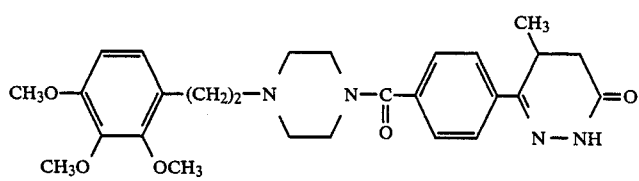

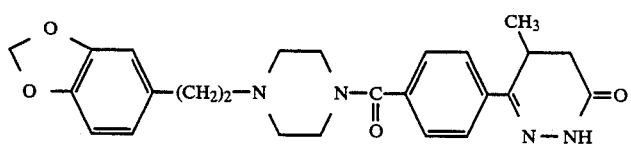

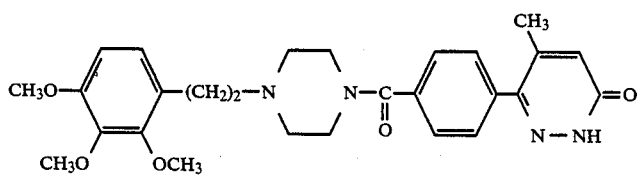

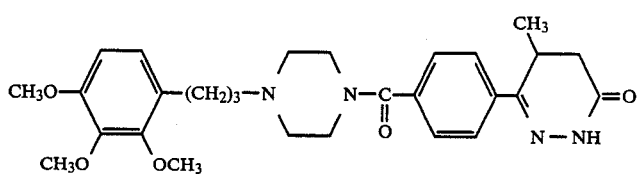

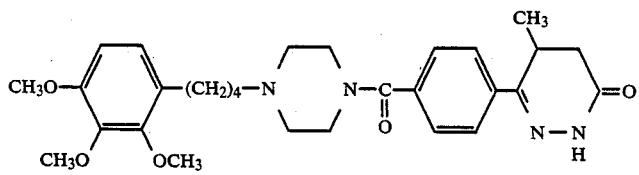

Though the compounds indicatively exemplified in the foregoing have the methyl group as the substituent R$_4$, the compounds in which R$_4$ is an ethyl, propyl, butyl, pentyl group or the like are also included within the compounds according to the present invention.

Furthermore, pharmaceutically accetable salts of the compounds as described above are also included in the scope of the present invention. As such salts, there can be mentioned a salt of mineral acid such as hydrochloric acid, sulfuric acid, hydrobromic acid, phosphoric acid and nitric acid, as well as a salt of organic acid such as lactic acid, acetic acid and oxalic acid. All of these compounds are useful as the cardiotonic and also have the vasodilative activity and blood pressure depressing activity.

In case of using the compound according to the invention as the cardiotonic, it may be administered in a suitable manner through an oral or parenteral route.

As the form of drug in the invention, there can be provided in the form of, for example, powder, granule, tablet, sugar-coated tablet, pill, capsule, solution and the like for the oral administration, and in the form of, for example, suppository, suspension, solution, emulsion, ampoule, injectable solution and the like for the parenteral administration. A combination of them may of course be provided as well.

The formulation may be conducted by a conventional manner in the art.

Further, a dose of the compound according to the present invention as the cardiotonic may be determined by a physician while considering age, sex, body weight and sensitivity of the patient, administration method, time and interval of the administration, degree of symptom, physical condition, properties, formulation and type of the pharmaceutical preparation, kind of the active ingredient and the like.

For instance, the dose of about 0.1 to 10 mg/kg per day per 1 kg of body weight may be selected for the oral administration, but it is, of course, on no account limitted thereto.

This invention will now be described more specifically referring to Examples, but the invention is on no account limitted only to the following Examples unless going beyond the scope of the gist thereof.

EXAMPLE 1
6-(4-(4-(4-methoxybenzyl)-1-piperazinylcarbonyl)-phenyl)-4,5-dihydro-5-methyl-3(2H)-pyridazin

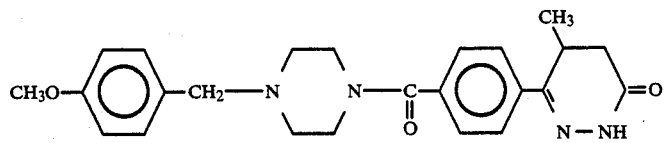

A mixture of 0.23 g of 4-(1,4,5,6-tetrahydro-4-methyl-6-oxo-3-pyridazinyl)benzene carboxylic acid, 0.5 ml of triethylamine solution in tetrahydrofuran (containing 0.10 g of triethylamine), 4 ml of N,N-dimethylformamide and 6 ml of tetrahydrofuran was cooled to −20° to −30° C. After cooling, a solution of ethyl chloroformate in tetrahydrofuran (containing 0.11 g of ethyl chloroformate) was added under stirring for about one minute.

After the addition and further stirring for 20 minutes under the same temperature, 3 ml solution of 0.21 g p-methoxybenzylpiperazine in dichloromethane was added at the same temperature.

Then, the temperature was gradually raised to a room temperature and, after one hour, 10 ml of tetrahydrofuran/methanol=1/1 was added to form a homogeneous mixture, and further 1 g of silica gel was added followed by concentrated to dry by an evaporator.

The silica gel having the thus obtained aimed product adsorbed thereon was placed in a column filled with 30 g of silica gel and subjected to the column chromatographic purification with chloroform/methanol mixed solvent (from chloroform alone to the ratio of 10/1).

Fractions containing the aimed product were evaporated and the obtained aimed product was dissolved into 5 ml of N,N-dimethylformamide and 10 ml of ethanol, to which 1.5 ml of 1N-hydrochloric acid/ethanol was added, and further 50 ml of ethyl ether and 50 ml of n-hexane were added, and deposited crystals were collected by filtration and dried to obtain a hydrochloric acid salt of the aimed 6-(4-(4-(4-methoxybenzyl)-1-piperazinylcarbonyl)phenyl)-4,5-dihydro-5-methyl-3(2H)-pyridazinone in an amount of 0.26 g (yield: 58%). IR: 1635 cm$^{-1}$.

EXAMPLE 2
6-(4-(4-(2,3,4-trimethoxybenzyl)-1-piperazinyl carbonyl)phenyl)-4,5-dihydro-5-methyl-3(2H)-pyridazinone

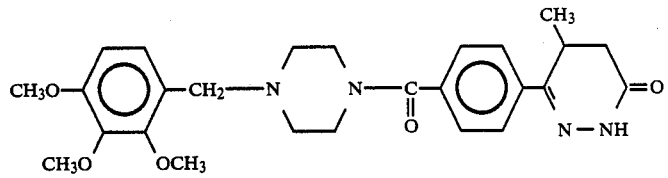

A mixture of 0.23 g of 4-(1,4,5,6-tetrahydro-4-methyl-6-oxo-3-pyridazinyl)benzene carboxylic acid, 0.5 ml of triethylamine solution in tetrahydrofuran (containing 0.10 g of triethylamine), 4 ml of N,N-dimethylformamide and 6 ml of tetrahydrofuran was cooled to −20° to −30° C. After cooling, a solution of ethyl chloroformate in tetrahydrofuran (containing 0.11 g of ethyl chloroformate) was added under stirring for about one minute.

After the addition and further stirring for 20 minutes under the same temperature, 3 ml solution of 0.27 g 2,3,4-trimethoxybenzylpiperazine in dichloromethane was added at the same temperature.

Then, the temperature was gradually raised to a room temperature and, after one hour, 10 ml of tetrahydrofuran/methanol=1/1 was added to form a homogeneous mixture, and further 1 g of silica gel was added followed by concentrated to dry by an evaporator.

The silica gel having the thus obtained aimed product adsorbed thereon was placed in a column filled with 30 g of silica gel and subjected to the column chromatographic purification with chloroform/methanol mixed solvent (from chloroform alone to the ratio of to 10/1).

Fractions containing the aimed product were evaporated and the obtained product was dissolved into 5 ml of N,N-dimethylformamide and 10 ml of ethanol, to which 1.5 ml of 1N-hydrochloric acid/ethanol was added, and further 50 ml of ethyl ether and 50 ml of n-hexane were further added, and the deposited crystals were collected by filtration and dried to obtain a hydrochloric acid salt of the aimed 6-(4-(4-(2,3,4-trimethoxybenzyl)-1-piperazinyl carbonyl)phenyl)-4,5-dihydro-5-methyl-3(2H)-pyridazinone in an amount of 0.21 g (yield: 41 %). IR: 1635 cm$^{-1}$.

TEST EXAMPLE

The usefulness of the compounds obtained in Examples 1 and 2 as a cardiotonic is demonstrated by means of standard pharmacological test methods, for example, by observing a significant increase in contraction of musculi papillares extracted from a dog and of left atrium muscle extracted from a guinea pig as well as by observing a significant increase in the cardiac contraction of an anaesthetized dog. Each pharmacological test method is described below.

1. Method of using an isolated cross-circulated papillary muscle preparation of the dog:

An isolated and cross-circulated papillary muscle preparation of the dog was prepared according to the method of Endo and Hashimoto, American Journal of Physiology, Vol. 218, 1459-1463 (1970), U.S.A. The compound dissolved in a solvent was intraarterially injected into the preparation and the effect on the contraction of the papillary muscle was recorded.

2. Method of using an isolated left atrium preparation of the guinea pig:

After striking the head of a male guinea pig with 200 to 300 g of body weight, the left atrium was immediately removed. The left mitral orifice was fixed to the bottom of an organ bath filled with 30 ml of Krebs-Henseleit solution maintained at 35° C. A gaseous mixture of 95% $O_2$ and 5% $CO_2$ was passed through the Krebs-Henseleit solution in the bath. Isometric tension was measured by connecting a thread to the left auricle of the heart and the other end of the thread to a transducer. A resting tension of 0.5 g was loaded to the preparation. Then the preparation was attached with two platinum electrodes and electrically driven by applying rectangular pulses of 1 msec in duration and of 1.5 × threshold voltage at a rate of twice per sec. After stabilizing the preparation for 30 minutes, the compound dissolved in a solvent was added to the bath and the effect was recorded.

3. Method of using anaesthetized dog:

Male or female mongrel dogs with body weight of 8 to 15 kg were used. The dogs were anaesthetized with 30 mg/kg of sodium pentobarbital (intravenous injection) and the artificial respiration was conducted. They were thoracotomized between the left fourth and fifth costae and the latter costa was removed. The pericardium was incised to expose the heart. Blood flow through the aorta was measured by attaching the probe of an electromagnetic flowmeter to the ascending aorta, which was used as an approximate index of cardiac output (CO). Left ventricular pressure was measured by inserting a catheter connected with a pressure transducer into the left ventricle and the rate of rise of the left ventricular pressure (dp/dt) was measured electrically. Contraction of the right ventricular wall (Cont) was determined with a strain-gauge attached to the wall of the right ventricle. Systemic blood pressure was measured from the left femoral artery. Heart rate was measured with electrocardiogram (lead II). The compound dissolved in a solvent was administered intravenously from the left femoral vein.

Upon conducting the pharmacological tests as described above, all of the cardiotonics according to the present invention caused the increase in the contraction of the papillary muscle of the dog and of the left atrium muscle of the guinea pig, as well as the increase in the maximum rate of rise of the left ventricular pressure (dp/dt max), Cont and CO, that is, the increase in the cardiac contraction of the anaesthetized dog. Table 1 shows the rate of increase in the contraction of the musculi papillares of the dog when the compound of the invention is administered by 30 μg, the rate of increase in the contraction of the left atrium of the guinea pig when administered by $10^{-5}$ g/ml and the rate of increase in dp/dt max, Cont and CO of the anaesthetized dog when administered by 10 and 30 μg/kg.

TABLE 1

| | Rate of Increase in Each Measured Value (%) | | | | | |
|---|---|---|---|---|---|---|
| Compound (Example No.) | Contraction of papillary muscle of dog (30 μg i.a.) | Contraction of left atrium muscle of guinea pig ($10^{-5}$ g/ml) | Anaesthetized dog | | | |
| | | | Dose (μg/Kg i.v.) | dp/dt max | Cont | CO |
| 1 | 23.0 | 41.7 | 10 | 28.7 | 28.7 | 13.2 |
| | | | 30 | 60.2 | 68.4 | 21.3 |
| 2 | 22.1 | 27.4 | 10 | 26.8 | 31.5 | 12.1 |
| | | | 30 | 70.2 | 78.6 | 22.4 |

INDUSTRIAL UTILITIES

The pyridazinone derivatives or the salts thereof according to the present invention are useful as the cardiotonic and also have the vasodilative activity and blood pressure depressing activity.

I claim:

1. A pyridazinone compound having the formula (I):

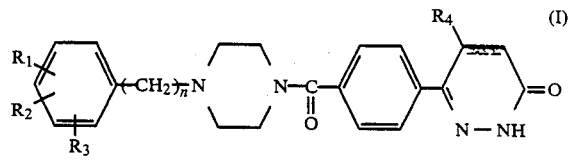

wherein $R_1$, $R_2$ and $R_3$ represent a hydrogen atom, hydroxy group or an alkoxy group of not more than 5 carbon atoms, or two of $R_1$, $R_2$ and $R_3$ at adjacent carbons are combined together to form a group of $-O-CH_2-O-$ or $-CH_2-O-CH_2-O-$, $R_4$ represents an alkyl group of not more than 5 carbon atoms, n represents an integer of 1 to 4 and the dotted line represents a single or double bond; or pharmaceutically-acceptable salts thereof.

2. The pyridazinone compound according to claim 1, wherein said pharmaceutically-acceptable salts are the salts of hydrochloric acid, sulfuric acid, hydrobromic acid, phosphoric acid, nitric acid, lactic acid, oxalic acid and acetic acid.

3. A cardiotonic pharmaceutical composition comprising an effective amount of one or more of the compounds of claim 1.

4. The pyridazinone compound according to claim 1, which is selected from the group consisting of compounds having the following formulas:
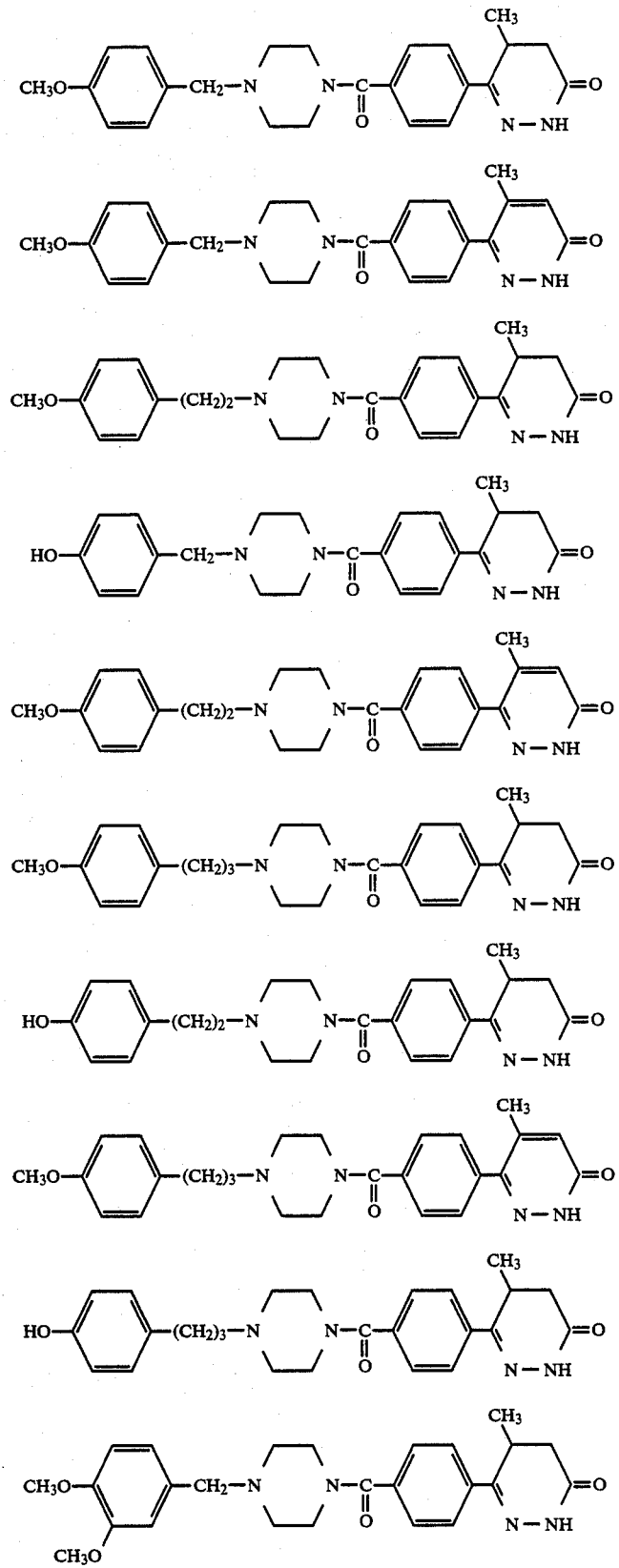

-continued
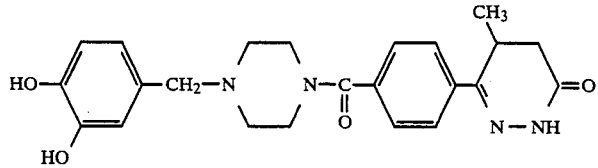
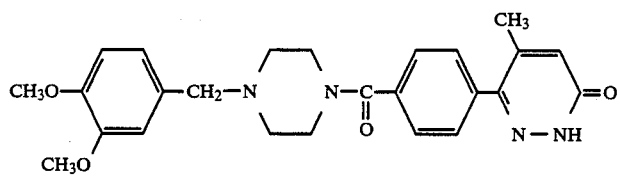
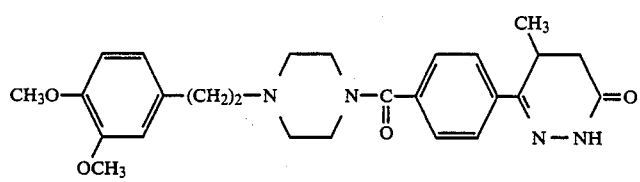
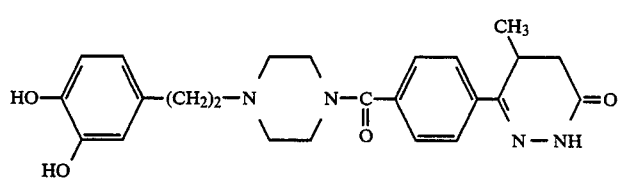
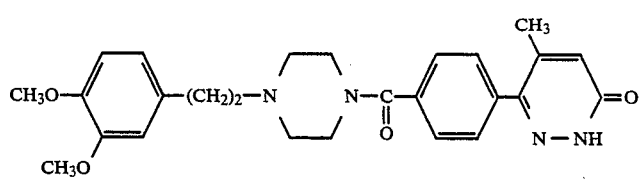
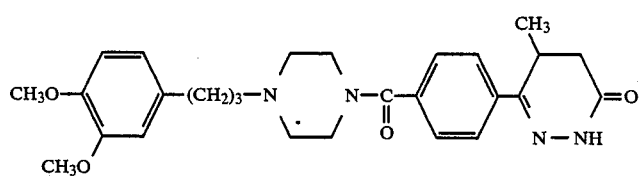
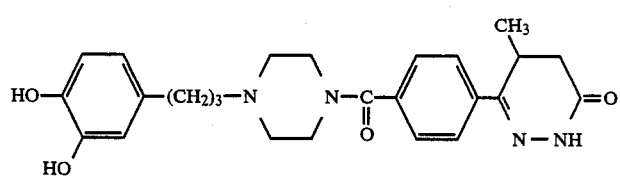
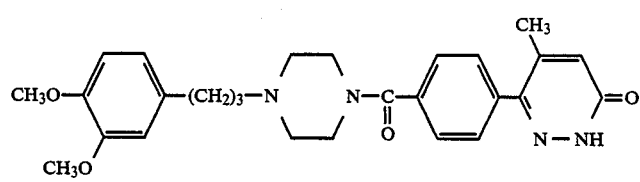
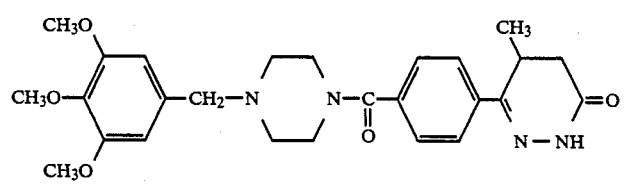

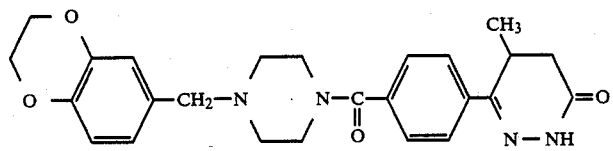
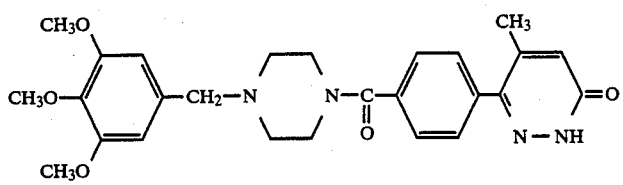
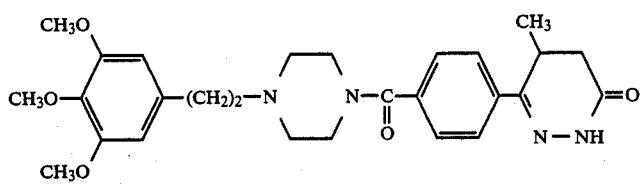
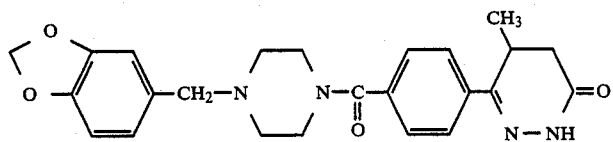
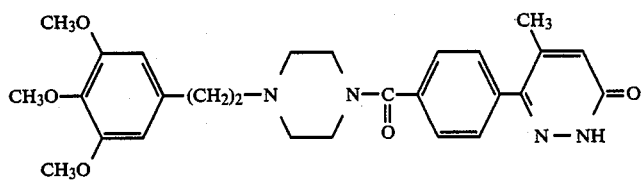
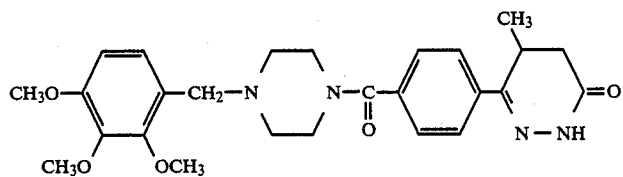
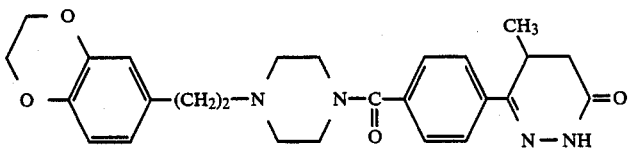
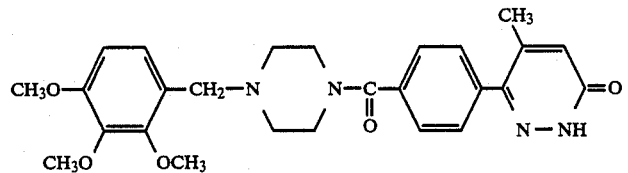
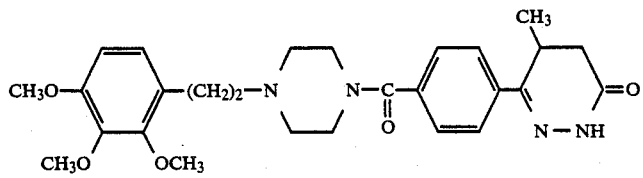

-continued
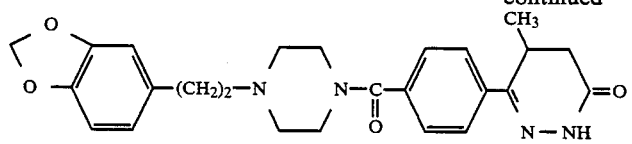
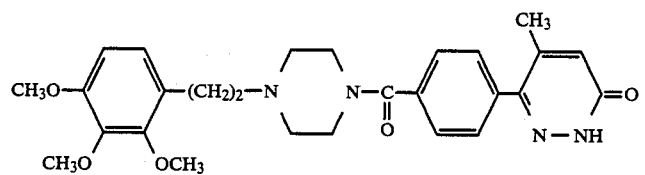
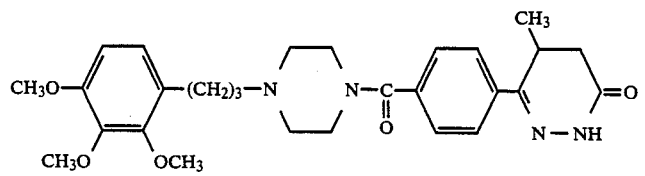
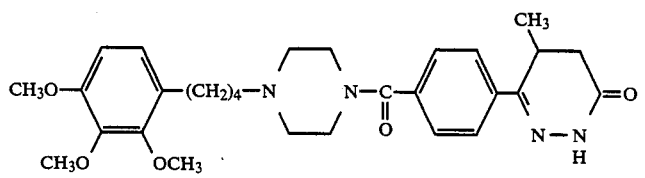
* * * * *